United States Patent
Gan et al.

(10) Patent No.: US 8,649,014 B2
(45) Date of Patent: Feb. 11, 2014

(54) VERTICAL PLASMONIC MACH-ZEHNDER INTERFEROMETER

(75) Inventors: Qiaoqiang Gan, Bethlehem, PA (US); Filbert Bartoli, Center Valley, PA (US)

(73) Assignee: Lehigh University

( * ) Notice: Subject to any disclaimer, the term of this patent is extended or adjusted under 35 U.S.C. 154(b) by 325 days.

(21) Appl. No.: 12/894,699

(22) Filed: Sep. 30, 2010

(65) Prior Publication Data

US 2011/0080589 A1    Apr. 7, 2011

Related U.S. Application Data

(60) Provisional application No. 61/248,114, filed on Oct. 2, 2009.

(51) Int. Cl.
*G01N 21/55* (2006.01)

(52) U.S. Cl.
USPC ............................ 356/445; 356/477; 356/481

(58) Field of Classification Search
USPC .................................. 356/450–521, 445–448
See application file for complete search history.

(56) References Cited

U.S. PATENT DOCUMENTS

| | | | |
|---|---|---|---|
| 6,710,870 B1 * | 3/2004 | Marowsky et al. | 356/317 |
| 7,399,445 B2 * | 7/2008 | Kuroda et al. | 422/504 |
| 2004/0130723 A1 * | 7/2004 | Yager et al. | 356/445 |
| 2006/0108219 A1 * | 5/2006 | Kuroda et al. | 204/403.1 |
| 2007/0258076 A1 * | 11/2007 | Maria Derksen et al. | 355/67 |
| 2009/0195783 A1 * | 8/2009 | Tazuke et al. | 356/445 |
| 2010/0103429 A1 * | 4/2010 | Cottier | 356/477 |
| 2012/0006981 A1 * | 1/2012 | Van Dorpe et al. | 250/227.11 |

OTHER PUBLICATIONS

Homola, J., Surface Plasmon Resonance Sensors for Detection of Chemical and Biological Species, Chem. Rev., 2008, 108:462-493.
Stewart, M.E., et al., "Nanostructured Plasmonic Sensors", Chem. Rev., 2008, 108:494-521.
Anker, J.N., et al., "Biosensing with Plasmonic Nanosensors", Nature Materials, Jun. 2008, 7:442-453.
Stewart, M.E., et al., "Quantitative multispectral biosensing and 1D imaging using quasi-3D plasmonic crystals", PNAS, Nov. 2006, 103(46):17143-17148.
Yang, J.C., et al., "Metalic Nanohole Arrays on Fluoropolymer Substrates as Small Label-Free Real-Time Bioprobes", Nano Letters, 2008, 8(9):2718-2724.
Tetz, K.A., et al., "High-resolution surface plasmon resonance sensor based on linewidth-optimized nanohole array transmittance", Optics Letters, May 2006, 31(10):1528-1530.

(Continued)

*Primary Examiner* — Tarifur Chowdhury
*Assistant Examiner* — Michael P LaPage
(74) *Attorney, Agent, or Firm* — The Belles Group, P.C.

(57) ABSTRACT

An optical device includes first and second optical branches. The first optical branch is formed at an interface between a first substrate and a second substrate, and the second optical branch is formed at an interface between the second substrate and an ambient medium. The second substrate defines first and second spaced apart slits that are each coupled to the first and second optical branches. The first slit is configured to receive at least partially coherent light from a light source and in response excite at least one surface plasmon polariton mode in each of the first and second optical branches. The second slit is configured to combine the surface plasmon polariton modes received from the first and second optical branches and emit scattered light into at least one of the first substrate and the ambient medium.

27 Claims, 4 Drawing Sheets

(56) References Cited

OTHER PUBLICATIONS

Lesuffleur, A., et al., Periodic nanohole arrays with shape-enhanced plasmon resonance as real-time biosensors, Applied Physics Letters, 2007, 90, 243110-1-3.

Brolo, A.G., et al., "Surface Plasmon Sensor Based on the Enhanced Light Transmission through Arrays of Nanoholes in Gold Films", Langmuir, 2004, 20:4813-4815.

Leebeeck, A.D., et al., "On-Chip Surface-Based Detection with Nanohole Arrays", Anal. Chem., 2007, 79(11):4094-4100.

Sharpe, J.C., et al., "Gold Nanohole Array Substrates as Immunobiosensors", Anal. Chem., 2008, 80(6):2244-2249.

Hwang, G.M., et al., "Plasmonic Sensing of Biological Analytes Through Nanoholes", IEEE Sensors Journal, Dec. 2008, 8(12):2074-2079.

Henzie, J., et al., "Multiscale patterning of plasmonic metamaterials", Nature Nanotech, Sep. 2007, 2:549-554.

Ji, J., et al., "High-Throughput Nanohole Array Based System to Monitor Multiple Binding Events in Real Time", Anal. Chem., 2008, 80(7):2491-2498.

Im, H., et al., "Plasmonic Nanoholes in a Multichannel Microarray Format for Parallel Kinetic Assays and Differential Sensing", Anal. Chem., 2008, 81(8):2854-2859.

Ji, J., et al., "Nanohole arrays of mixed designs and microwriting for simultaneous and multiple protein binding studies", Biosensors and Bioelectronics, 2009, 24:2847-2852.

Braun, D., et al., "Fluorescence Interferometry of Neuronal Cell Adhesioin on Microstructured Silicon", Physical Review Letters, Dec. 1998, 81(23):5241-5244.

Moiseev, L., et al., "DNA conformation on surfaces measured by fluorescence self-interference", PNAS, Feb. 2006, 103(8):2623-2626.

Bilenca, A., et al., "Fluorescence Interferometry, Principles and Applications in Biology", Ann. N.Y. Acad. Sci., 2008, 1130:68-77.

Dogan, M., et al., "Spectral Self-Interference Fluorescence Microscopy for Subcellular Imaging", IEEE Journal of Selected Topics in Quantum Electronics, Jan./Feb. 2008, 14(1):217-225.

Shtengel, G., et al., "Interferometric fluorescent super-resolution microscopy resolves 3D cellular ultrastructure", PNAS, Mar. 2009, 106:3125-3130.

Brosinger, F., et al., "A label-free affinity sensor with compensation of unspecific protein interaction by a highly sensitive integrated optical Mach-Zehnder interferometer on silicon", Sensors and Actuators B Chem., 1997, 44:350-355.

Prieto, F., et al., "An integrated optical interferometric nanodevice based on silicon technology for biosensor applications", Nanotechnology, 2003, 14:907-912.

Prieto, F., et al., "Integrated Mach-Zehnder interferometer based on ARROW structures for biosensor applications", Sensors and Actuators B Chem., 2003, 92:151-158.

Schipper, E.F., et al., "The realization of an integrated Mach-Zehnder waveguide immunosensor in silicon technology", Sensors and Actuators B Chem., 1997, 40:147-153.

Ymeti, A., et al., "Realization of a multichannel integrated Young interferometer chemical sensor", Applied Optics, Oct. 2003, 42(28):5649-5660.

Swann, M.J., et al., "Dual-polarization interferometry: an analytical technique to measure changes in protein structure in real time, to determine the stoichiometry of binding events, and to differentiate between specific and nonspecific interactions", Analytical Biochemistry, 2004, 329:190-198.

Bornhop, D.J., et al.,, "Free-Solution, Label-Free Molecular Interactions Studied by Back-Scattering Interferometry", Science, Sep. 2007, 317:732-736.

Ozkumur, E., et al., "Label-free and dynamic detection of biomolecular interactions for high-throughput microarray applications", PNAS, Jun. 2008, 105(23):7988-7992.

Schouten, H.F., et al., "Plasmon-Assisted Two-Slit Transmission: Young's Experiment Revisited", Physical Review Letters, Feb. 2005, 94:053901-1-4.

Temnov, V.V., et al., "Surface plasmon interferometry: measuring group velocity of surface plasmons", Optics Letters, May 2007, 32(10):1235-1237.

Wu, X., et al., "Refractive index sensor based on surface-plasmon interference", Optics Letters, Feb. 2009, 34 (3):392-394.

Lee, M.H., et al., "Refractive Index Sensing Using Quasi One-Dimensional Nanoslit Arrays", Nano Letters, 2009, 9 (7):2584-2588.

Lalanne, P., et al., "A microscopic view of the electromagnetic properties of sub-A metallic surfaces", Surf. Sci. Rep., 2009, 37 pages.

Fu, Z., et al., "Numerical Investigation of a Bidirectional Wave Coupler Based on Plasmonic Bragg Gratings in the Near Infrared Domain", Journal of Lightwave Technology, Nov. 2006, 26(22):3699-3703.

Gan, Q., et al., "Ultrawide-Bandwidth Slow-Light System Based on THz Plasmonic Graded Metallic Grating Structures", Physical Review Letters, Jun. 2008, 100:256803-1-4.

Gan, Q., et al., ""Rainbow" Trapping and Releasing at Telecommunication Wavelengths", Physical Review Letters, Feb. 2009, 102:056801-1-4.

Lalanne, P., et al., "Approximate model for surface-plasmon generation at slit aperatures", J. Op. Soc. Am. A., Jul. 2006, 23(7):1608-1615.

Kihm, H.W., et al., "Control of surface plasmon generation efficiency by slit-width tuning", Applied Physics Letters, 2008, 92:05115-1-3.

Drezet, A., et al., "How to erase surface plasmon fringes", Applied Physics Letters, 2006, 89:091117-1-3.

Lalanne, P., et al., "Interaction between optical nano-objects at metallo-dielectric interfaces", Nature Physics, Aug. 2006, 2:551-556.

Garcia de Abajo, F. J., et al., "Colloquium: Light scattering by particle and hole arrays", Rev. Mod. Phys., Oct.-Dec. 2007, 79:1267-1290.

Weiner, J., "The physics of light transmission through subwavelength apertures and aperture arrays", Rep. Prog. Phys., 2009, 72:064401-1-19.

\* cited by examiner

VERTICAL PLASMONIC MACH-ZEHNDER INTERFEROMETER

CROSS-REFERENCE TO RELATED APPLICATIONS

This application claims priority to U.S. Provisional Patent Application No. 61/248,114, which was filed on Oct. 2, 2009, and the entirety of which is herein incorporated by reference.

STATEMENT OF GOVERNMENTAL INTEREST

This invention was made with Government support from the National Science Foundation—Bioengineering & Environmental Systems under award 0608742, the National Science Foundation—Electrical, Communications and Cyber Systems under award 0901324, and from the Department of Defense-Army Research Laboratories, Army Optics V and VI. The Government may have certain rights in this invention.

FIELD OF DISCLOSURE

The disclosed system and method relate to interferometry. More specifically, the disclosed system and method relate to interferometry utilizing a vertical plasmonic Mach-Zehnder interferometer.

BACKGROUND

Interferometry is one of the most sensitive optical interrogation methods and has been used in a wide array of technologies including astronomy, fiber optics, engineering metrology, quantum mechanics, plasma physics, remote sensing, and biomolecular interactions such as screening molecular interactions in surface binding modes. Several types of interferometry have been developed such as fluorescence interferometry for high resolution microscopy or nanoscopy, label-free sensing based on a Mach-Zehnder Interferometer, a Young Interferometer, a dual polarization interferometer, back-scattering interferometry, and spectral reflectance interferometry, to name a few.

Surface Plasmons ("SPs") are coherent oscillations of conduction electrons on a metal surface excited by electromagnetic radiation at a metal-dielectric interface. The sensitivity of the Surface Plasmon Resonance ("SPR") to the refractive index change at a flat metal interface has led to the development of SPR sensing systems based on interferometry and that use prisms to couple light into a single surface-plasmon mode on a flat, continuous metal film (e.g., gold). However, the relatively large size of these experimental systems is a disadvantage for applications requiring integrated, low-cost, compact, image-based devices for portable, rapid bio-analytical measurements.

Nanoplasmonic biosensors, employing nanoscale metal particles, provide an attractive miniaturized platform for sensitive, label-free monitoring of cellular processes. When receptor molecules are immobilized on the nanostructured metal surface, the binding of target biomolecules changes the local refractive index, which affects the optical properties of the SP modes and permits optical detection. Recent advances in nanofabrication, nanomaterial synthesis, and nanocharacterization permit significant advances over conventional SPR evanescent wave-based biosensors, whose large size limits their effectiveness for probing nanovolumes and single cells, and for integration into microfluidic platforms. However, the sensitivities for these nanoplasmonic structures are much lower (two to three orders of magnitude) than other sensitive optical sensing technologies.

SUMMARY

An optical device is disclosed that includes first and second optical branches. The first optical branch is formed at an interface between a first substrate and a second substrate, and the second optical branch is formed at an interface between the second substrate and an ambient medium. The second substrate defines first and second spaced apart slits that are each coupled to the first and second optical branches. The first slit is configured to receive at least partially coherent light from a light source and in response excite at least one surface plasmon polariton mode in each of the first and second optical branches. The second slit is configured to combine the surface plasmon polariton modes received from the first and second optical branches and emit scattered light into at least one of the first substrate and the ambient medium.

Also disclosed is an optical device that includes a first substrate having opposed first and second surfaces. The first substrate is configured to transmit light received at the first surface to the second surface. A second substrate has opposed third and fourth surfaces with the third surface of the second substrate disposed on the second surface of the first substrate to define a first interface. The fourth surface of the second substrate defines a second interface with an ambient medium, and the second substrate defines spaced apart first and second slits that extend from the third surface to the fourth surface. The first slit is configured to excite at least one first surface plasmon polariton mode along a first optical transmission path defined by the first interface and at least one second surface plasmon polariton mode along a second optical transmission path defined by the second interface in response to receiving the light through the first substrate. The second slit is configured to combine the at least one first and second surface plasmon polariton modes received from the first slit and emit scattered light into one of the first substrate and the ambient medium.

A method is also disclosed in which at least partially coherent light is received at a first surface of a first substrate, and the at least partially coherent light is transmitted from the first surface of the first substrate to a second surface of the first substrate. At least one first surface plasmon polariton mode is excited along a first optical transmission path defined by an interface of the first substrate and a second substrate in response to receiving the partially coherent light at a first slit defined by the second substrate, and at least one second surface plasmon polariton mode is excited along a second optical transmission path defined by an interface of the second substrate and a surrounding medium in response to receiving the partially coherent light at the first slit. The at least one first and second surface plasmon polariton modes are combined at a second slit defined by the second substrate, and light is scattered into at least one of the first substrate and the ambient medium.

DETAILED DESCRIPTION

This description is intended to be read in connection with the accompanying drawings, which are to be considered part of the entire written description. The drawing figures are not necessarily to scale and certain features may be shown exaggerated in scale or in somewhat schematic form in the interest of clarity and conciseness. In the description, relative terms such as "horizontal," "vertical," "up," "down," "top" and "bottom" as well as derivatives thereof (e.g., "horizontally," "downwardly," "upwardly," etc.) should be construed to refer to the orientation as then described or as shown in the drawing figure under discussion. These relative terms are for convenience of description and normally are not intended to require a particular orientation. Terms including "inwardly" versus "outwardly," "longitudinal" versus "lateral" and the like are to be interpreted relative to one another or relative to an axis of elongation, or an axis or center of rotation, as appropriate. Terms concerning attachments, coupling and the like, such as "connected" and "interconnected," refer to a relationship wherein structures are secured or attached to one another either directly or indirectly through intervening structures, as well as both movable or rigid attachments or relationships, unless expressly described otherwise. When only a single machine is illustrated, the term "machine" shall also be taken to include any collection of machines that individually or jointly execute a set (or multiple sets) of instructions to perform any one or more of the methodologies discussed herein. The term "operatively connected" is such an attachment, coupling or connection that allows the pertinent structures to operate as intended by virtue of that relationship. In the claims, means-plus-function clauses, if used, are intended to cover the structures described, suggested, or rendered obvious by the written description or drawings for performing the recited function, including not only structural equivalents but also equivalent structures.

A vertical plasmonic Mach-Zehnder interferometer ("VPMZI") is disclosed that provides high sensitivity optical sensing. The VPMZIs disclosed herein enable optical microscopes to perform Surface Plasmon Resonance ("SPR") sensing thereby eliminating the need for the conventional bulky and expensive angular tunable systems. The flexibility provided by the VPMZIs advantageously enables future microscopes to integrate SPR sensing functionality, which should have significant commercial potential. Additionally, the compact package of the VPMZIs disclosed herein may be integrated into sensitive biosensing platforms and subwavelength optics on a chip.

Figure 1:
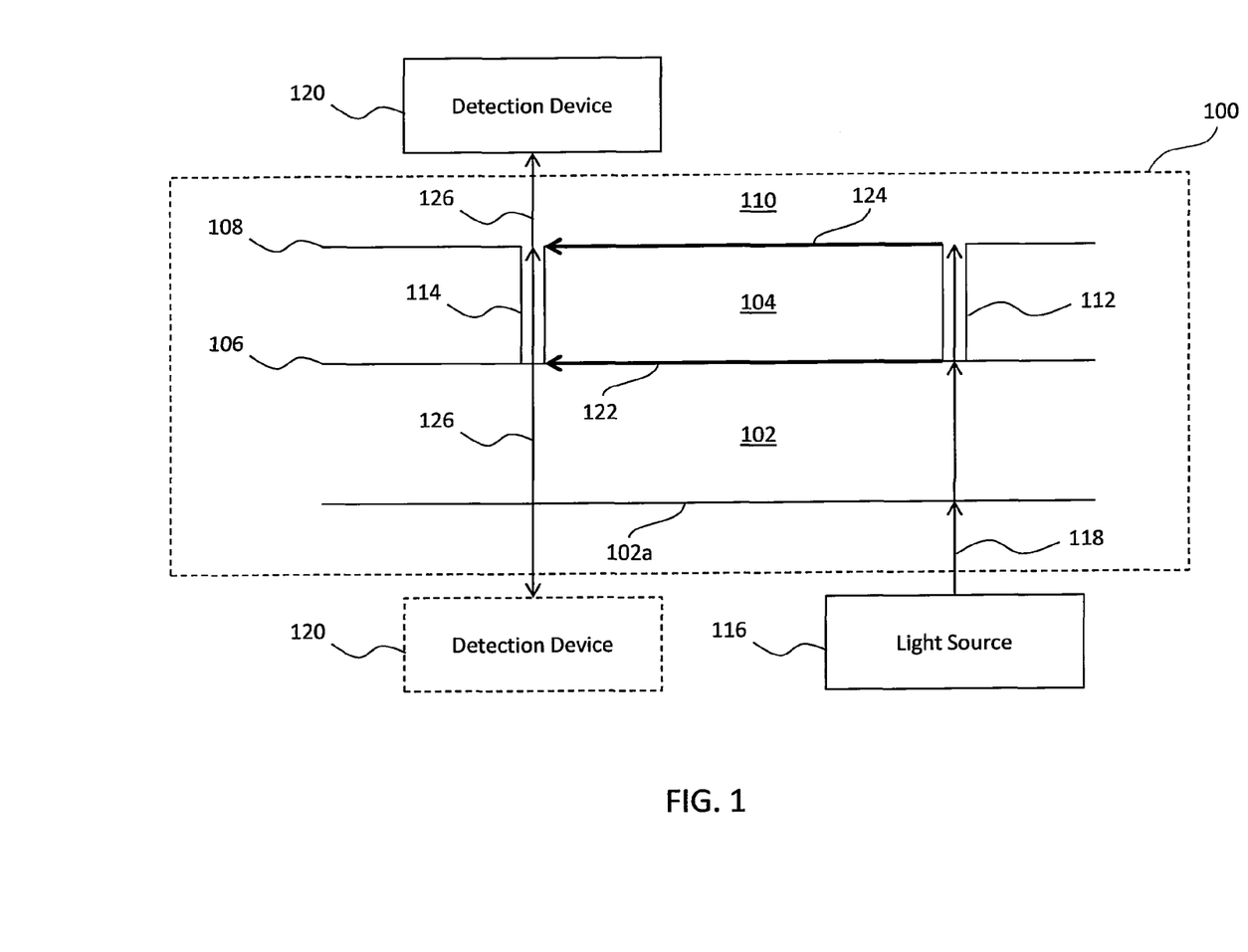
FIG. 1 illustrates one example of a vertical plasmonic Mach-Zehnder interferometer.

The VPMZI 100 illustrated in FIG. 1 includes a first substrate 102 on which a second substrate 104 is disposed. A first interface 106 is defined between substrate 102 and substrate 104, and a second interface 108 is defined by substrate 104 and ambient medium 110. Second substrate 104 defines first and second slits 112, 114, which are horizontally spaced apart from one another. A light source 116 may be configured to direct light 118 towards first slit 112, and a detection device 120 may be configured to receive light 122 from second slit 114.

Substrate 102 is fabricated from glass and may have a variety of thicknesses and widths. Examples of substrate 102 include, but are not limited to, glass, Quartz, and other transparent semiconductor substrates.

Substrate 104 is a metal-containing layer having a thickness approximately on the order of tens or hundreds of nanometers depending on the material from which substrate 104 is fabricated. Such materials include, but are not limited to, gold, silver, copper, and aluminum, to name only a few possible materials. Substrate 104 may be deposited on substrate 102 in a variety of methods including, but not limited to, chemical vapor deposition ("CVD"), atomic layer deposition ("ALD"), electroless plating, and sputtering and evaporation.

Slits 112 and 114 may be formed in substrate 104 by utilizing a wide variety of methods, such as focused ion beam ("FIB") milling, electron beam ("e-beam") lithography, and nano-imprint lithography. The thicknesses of slits 112 and 114 are on the order of one to several hundreds of nanometers and may vary depending on the material used for substrate 104 in order to couple visible and near visible infrared light. For example, if substrate 104 is a 200 nm-thick silver film deposited on a glass substrate and includes two parallel slits 112 and 114 that are separated from each other by approximately 97 μm, then slits 112 and 114 may be approximately 100 nm wide and 40 μm long for use with wavelengths between 800 and 900 nm. Slits 112 and 114 may also be disposed from one another at various distances on the order of several microns to tens of microns and beyond.

Interface 106 between substrate 102 and substrate 104 defines a first optical branch or optical transmission path capable of supporting at least one surface plasmonic polariton ("SPP") mode. Similarly, interface 108 between substrate 104 and ambient medium 110 defines a second optical branch capable of supporting at least one SPP mode having a different phase than the SPP mode of interface 106. Medium 110 may be a dielectric material in the form of a solid, liquid, or gas. In some embodiments in which VMZI 100 is integrated into a biologic sensing device, medium 110 is a liquid, such as water, that includes a sample of biologic material to be tested, and in some embodiments, medium 110 is air. However, one skilled in the art will understand that VPMZI 100 may be disposed within a variety of different mediums for testing.

Light source 116 may be any light source that provides light 118 that is at least partially coherent. For example, light source 116 may be a halogen lamp, light emitting diode ("LED"), or a laser, to name a few possible partially coherent light sources. Light source 116 may be disposed adjacent to substrate 102 such that light 118 emitted by light source 116 contacts a surface 102a of substrate 102, which is on the opposite side of substrate 102 as interface 106. Light 118 may be emitted from light source 116 such that it is parallel to a plane defined by surface 102a of substrate 102 and is approximately aligned with an axis defined by slit 112 defined by substrate 104. In some embodiments, light source 116 emits light 118 at an angle other than a right angle with respect to a plane defined by surface 102a of substrate 102. Additionally, a polarizer (not shown) may be coupled to the light source 116 to polarize the at least partially coherent light 118 emitted by light source 116. For example, the polarizer may polarize light 118 such that light 118 is perpendicular to slits 112 and 114.

Detection device 120 may be any device configured to detect optical signals emitted from slit 114 either through ambient medium 110 (shown in FIG. 1 as solid rectangle) or through substrate 102 (shown in FIG. 1 as dotted rectangle). Examples of detection devices 120 include, but are not limited to, spectrometers, monochromators, charged coupled device ("CCD") or complimentary metal-oxide semiconductor ("CMOS") image sensors. In some embodiments, detection device 120 may be a spectrum analyzer configured to receive and perform spectral analysis on the optical signals emitted from slit 114.

In operation, light source 116 emits at least partially coherent light 118 towards surface 102a of substrate 102. As described above, light 118 may be transmitted by light source 116 such that light 118 is emitted at an angle that is orthogonal to a plane defined by surface 102a, or light 118 may be transmitted by light source 116 at an angle other than ninety degrees with respect to a plane defined by surface 102a. Regardless of the angle at which light 118 is emitted with respect to the plane defined by surface 102a, light 118 is directed towards one of the slits 112, 114 defined by substrate 104.

The light 118 received at surface 102a of substrate 102 is transmitted through substrate 102 to interfaces 106 and 108 of substrate 102 at or near a location of one of the slits 112, 114 (in this example at slit 112). One or more SPP modes 122 and 124 are excited in each of the optical transmission paths defined by interfaces 106 and 108 in response to receiving light 118 from light source 116. SPP modes 122 and 124 propagate towards slit 114 where they constructively and destructively interfere with one another.

The interference of SPP modes 122 and 124 at slit 114 results in scattered light 126 being emitted from slit 114 toward ambient medium 110 and back into substrate 102. Detection device 120 may be positioned adjacent to substrate 104 or substrate 102 such that it receives scattered light 126. The interference pattern of the far-field scattering of SPP modes 122 and 124 includes the following term:

$$\cos\left[\frac{2\pi L}{\lambda}\left(\sqrt{\frac{e'_m(\lambda)n_{110}^2}{e'_m(\lambda)+n_{110}^2}} - \sqrt{\frac{e'_m(\lambda)n_{102}^2}{e'_m(\lambda)+n_{102}^2}}\right)\right] \quad \text{Eq. (1)}$$

Where, $\in'_m$ is the real part of the permittivity of substrate 104;

$n_{110}$ is the refractive index of the ambient dielectric medium 110 adjacent to substrate 104;

$n_{102}$ is the refractive index of substrate 102;

L is the slit separation distance, i.e., the distance between slits 112 and 114;

$\lambda$ is the wavelength of the partially coherent light; and $$\sqrt{\frac{e'_m(\lambda)n^2}{e'_m(\lambda)+n^2}}$$

is the effective refractive index ("ERI") of interface 108 between substrate 104 and ambient medium 110.

Notably, the two optical branches defined by interfaces 106 and 108 of VPMZI 100 may be separated by a gap that is only several hundred nanometers wide (i.e., the thickness of substrate 104 may be on the order of hundreds of nanometers), which is appreciably smaller than for silicon-based planar MZIs.

The phase modulation properties of VPMZI 100 are sensitive to changes in the refractive index in the sensing transmission path 108 relative to the refractive index in the reference transmission path 106. When the refractive index of the sensing transmission path 108, which is determined by the refractive index of ambient medium 110, $n_{110}$, is changed to $n_{110}+\Delta n_{110}$, the phase change is given by the following equation:

$$\Delta\varphi = \frac{2\pi L}{\lambda}\left(\sqrt{\frac{e'_m(\lambda)n_{110}^2}{e'_m(\lambda)+n_{110}^2}} - \sqrt{\frac{e'_m(\lambda)(n_{110}+\Delta n_{110})^2}{e'_m(\lambda)+(n_{110}+\Delta n_{110})^2}}\right) \quad \text{Eq. (2)}$$

Figure 2A:
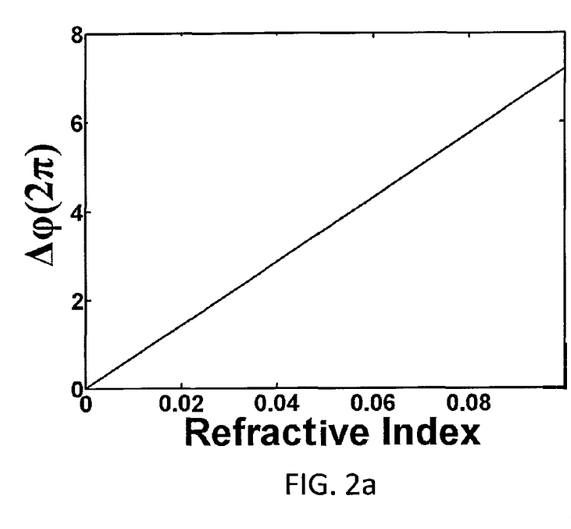
FIG. 2a illustrates the phase modulation properties of a vertical plasmonic Mach-Zehnder interferometer in accordance with FIG. 1.
Figure 2B:
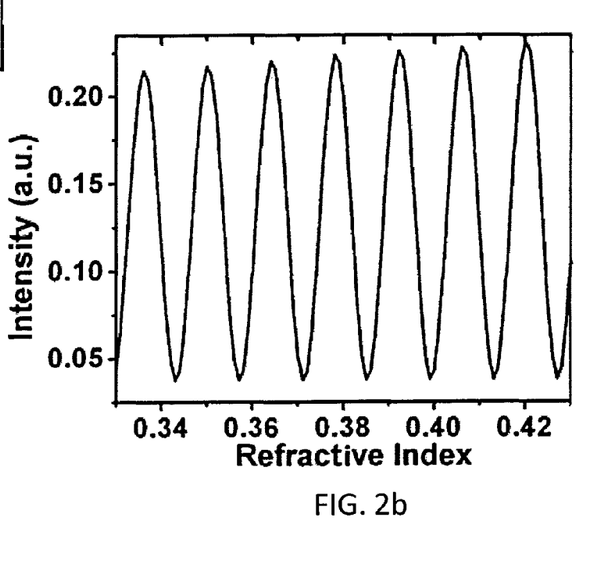
FIG. 2b illustrates a simulated intensity modulation of an output signal from a vertical plasmonic Mach-Zehnder in accordance with FIG. 1.

Equation 2 can be used to analyze the relation between the phase change and the refractive index change. In this calculation, an incident wavelength of 1033 nm is employed, for which the permittivity of silver (−48.81+i3.16) is used as substrate 104. Assuming that the ambient medium 110 is water ($n_{110}$=1.33) and the distance between slits 112 and 114, a refractive index change of 0.1 may introduce a phase change of about 7.2 (2π) as shown in FIG. 2a, which is in a good agreement with the two-dimensional ("2D") finite-difference-time-domain ("FDTD") modeling result shown in FIG. 2b. Based on the FDTD modeling result, more than seven periods of interference pattern can be observed in the far-field scattering signal, which can be utilized in optical sensing applications. The length of the sensing transmission path 108 is kept relatively short to minimize the intrinsic loss of metals. For example, transmission paths 106 and 108 may be on the order of tens of microns to hundreds of microns, although one skilled in the art will understand that transmission paths 106 and 108 may have other lengths. Consequently, the phase-change sensitivity of this metallic VPMZI (approximately 72(2π)/refractive index unit ("RIU")) is much lower than Si-based MZIs with long sensing arms. For example, the phase-change sensitivity of a Si-based MZI with a 5 mm sensing arm is reported to be about 1400(2π)/RIU.

The double-slit or slit-groove metal VPMZI device 100 can also support spectral interference when the input is a broad band light source. Spectral interference is supported by the proposed VPMZI, which provides an ultrahigh sensitivity that is significantly better than has been reported for other nanoplasmonic architectures. For example, when the refractive index or the ambient medium 110 is changed, the peaks and valleys in the interference pattern will shift. The sensitivity may be derived by setting the right side of Equation 2 to a constant value, which yields the following equation:

$$S = \frac{\Delta\lambda}{\Delta n} \quad \text{Eq. (3)}$$

$$= \frac{\lambda}{n'_m}\left(\frac{e'_m(\lambda)n_{110}^2}{e'_m(\lambda)+n_{110}^2}\right)^{3/2} \Big/ \left(\sqrt{\frac{e'_m(\lambda)n_{110}^2}{e'_m(\lambda)+n_{110}^2}} - \sqrt{\frac{e'_m(\lambda)n_{102}^2}{e'_m(\lambda)+n_{102}^2}}\right)$$

Figure 3:
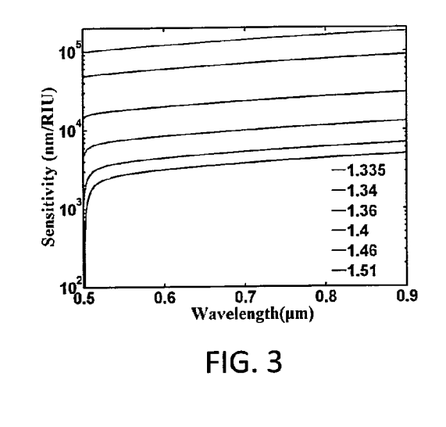
FIG. 3 illustrates a sensitivity versus wavelength graph demonstrating the theoretical sensitivity of a vertical plasmonic Mach-Zehnder interferometer in accordance with FIG. 1.

From Equation 3, it is seen that when $n_{110}$<$n_{102}$, the sensitivity value is negative, indicating that the interference pattern will shift to shorter wavelengths, whereas if $n_{110}$>$n_{102}$, then the sensitivity value is positive, indicating that the interference pattern will shift to longer wavelengths. Equation 3 also provides that the sensitivity increases if the two terms in the denominator are close in value. FIG. 3 illustrates the sensitivities that could potentially be achieved by varying the refractive index of the material of substrate 102. In this calculation, substrate 104 is gold and ambient medium 110 is water ($n_{110}=1.33$).

As an example, when $n_{102}=1.51$, the relation between the sensitivity and the operating wavelength is shown by the lowest curve in FIG. 3. The sensitivity cannot be enhanced by orders or magnitude by employing longer wavelengths. However, when the refractive index of substrate 102, $n_{102}$, is decreased and approaches that of ambient medium 110, $n_{110}$, the sensitivity can increase significantly as illustrated by the series of curves in FIG. 3.

Matching the ERI at of substrate 102 and ambient medium 110 increases the sensitivity of VPMZI 100. In one embodiment, the ERI matching condition is where the dispersion curve at the interface 108 is approximately equal to the dispersion curve at interface 106, which indicates that the ERI match condition could be met over a broad range of wavelengths. This can in principle be accomplished by providing a substrate 102 having a refractive index that is close to the refractive index of ambient medium 110. For example, fluorinated ethylene propylene copolymer (FEr) may be implemented as substrate 102 because it is chemically inert, thermoplastic, transparent in the visible region, and has a refractive index of 1.341 at the $\lambda$ of 590 nm.

Figure 4:
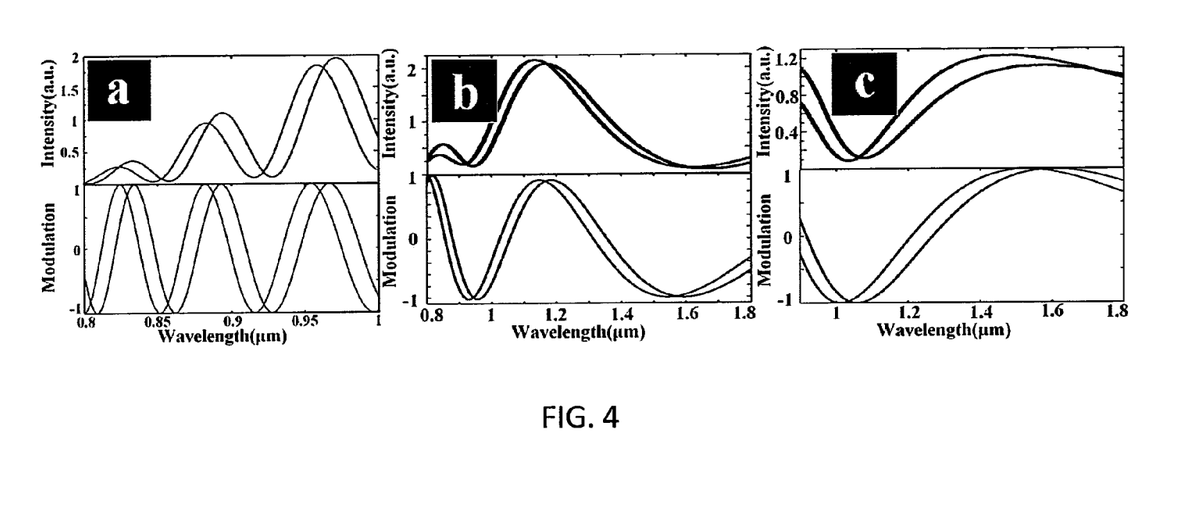
FIGS. 4a-4c illustrate numerical modeling for an interference signal of the scattered light from a slit in Au film in accordance with the vertical plasmonic Mach-Zehnder interferometer illustrated in FIG. 1 for various refractive indices.

A 2D FDTD method was used to simulate the sensitivity for a gold substrate 108 disposed on substrates 102 having various refractive index values for a VPMZI 100 in accordance with FIG. 1 in which slits 112 and 114 were separated by approximately 70 μm and only slit 112 was illuminated by the incident light. The sensitivity from the shift in the peak or valley wavelength was calculated for a variety of different refractive indices. For example, if $n_{102}=1.46$, then when $n_{110}$ changes from 1.33 to 1.331, the peak of the interference pattern at 970 nm will shift to 964 nm, which indicates that the sensitivity is $-0.6\times10^4$ nm/RIU (see the upper panel in FIG. 4a). If $n_{102}$ is set to 1.36, then the valley of the interference pattern at 940 nm shifts to 908 nm, which indicates a sensitivity of about $-3.2\times10^4$ nm/RIU. Similarly, the peak at 1168 nm shifts to 1132 nm, which indicates a sensitivity of about $-3.6\times10^4$ nm/RIU as shown in the upper panel of FIG. 4b. Further decreasing $n_{102}$ to 1.35 provides a shift in the valley position from 1076 nm to 1034 nm, which indicates a sensitivity of $-4.2\times10^4$ nm/RIU. At the same time, the peak at 1582 nm, shifts to 1486 nm, which indicates a sensitivity of about $-9.2\times10^4$·nm/RIU as shown in the upper panel of FIG. 4c. In accordance with the expression on the right side of Equation 2, the theoretical spectral interference pattern of this structure was calculated and plotted in the lower panels in FIGS. 4a-4c, which is in accordance with the FDTD modeling result. Remarkably, the sensitivities shown in FIGS. 4b and 4c are between one and two orders of magnitude larger than the best sensitivity previously reported for nanohole arrays (approximately 1500 nm/RIU).

If a low refractive index substrate is unavailable, then the ERI matching condition can also be met by various surface dispersion engineering approaches. For example, one can introduce a thin film of dielectric material with a higher refractive index on substrate 104 at interface 108 between substrate 104 and ambient medium 110 to tune the ERI of this interface. Various nanopatterned structures, such as periodic metal-dielectric-air grooves and surface grating structures can be employed to finely tune the shape of the dispersion curve and approach to the ERI match condition.

Experimental Setup

An experiment was performed to determine if spectral interference of light emitted from slot 114 is observable. The optical transmission measurements were performed on an IX81® inverted microscope available from Olympus America Inc. of Center Valley, Pa. using a white light beam 118 from a 100 W halogen lamp that was focused at nominal incidence onto surface 102a of substrate 102, which was a glass substrate, through the microscope condenser with a linear polarizer. The polarization of the incident light was transverse magnetic ("TM") with respect to the longitudinal axis of slit 112. The transmission light was collected by an X40 microscope objective with a numerical aperture of 0.6 coupled into a multimode fiber bundle connected with a fiber-based compact spectrometer, which was a USB4000 fiber optic spectrometer available from Ocean Optics, Inc. of Dunedin, Fla.

Figure 5:
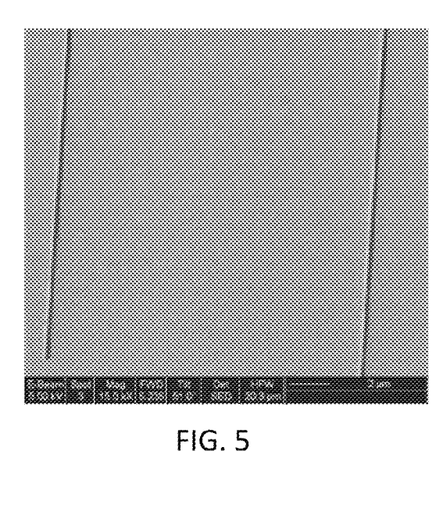
FIG. 5 is a scanning electron microscope image of a pair of slits formed on a metal substrate.

A charge coupled device ("CCD") camera was employed to align the position of the double slits. Consequently, the collection condition of the transmitted light from all the samples is almost identical. A diaphragm in the condenser was employed to minimize the intensity of the light beam illuminating the other slit 114. Several VPMZIs in accordance with FIG. 1 were fabricated using by creating slits 112 and 114 at various distances in 300 nm-thick layers of gold and silver (substrate 104) that were evaporated onto a flat fused silica microscope slide (substrate 102). Slits 112 and 114, which had a thickness of approximately 220 nm, were formed by FIB milling substrate 104 with a DualBeam™ 235 available from FEI Company of Hillsboro. Four samples on a silver film with slit-slit separation distances of 10.50, 13.12, 15.73 and 20.98 μm were observed and studied. A scanning electron microscope image of a VPMZI 100 having a slit-slit separation distance of 15.73 μm with slits 112 and 114 having widths of approximately 220 nm is shown in FIG. 5.

Experimental Results

Figure 6:
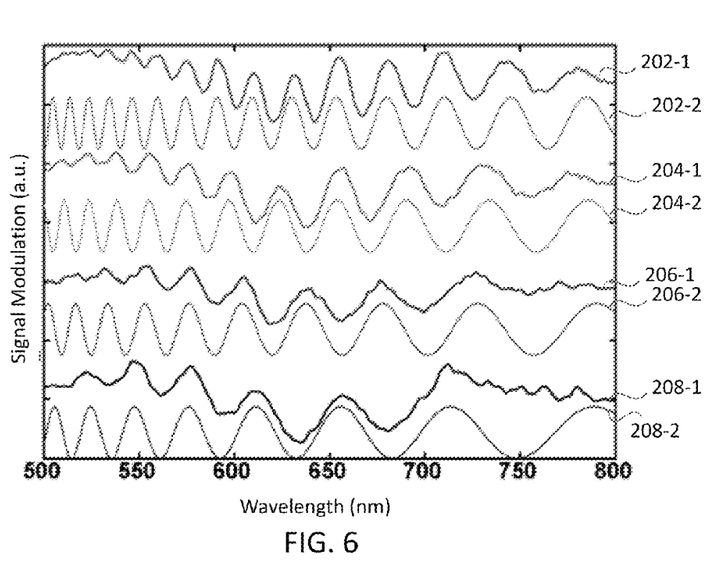
FIG. 6 illustrates SPP-mediated spectral interference introduced by SPP from first and second interfaces of a vertical Mach-Zehnder interferometer in accordance with FIG. 1.

The measurement results are shown by bold solid lines 202-1, 204-1, 206-1, and 208-1 in FIG. 6 in which spectral interference patterns can be observed under the TM illumination. The low frequency background and high frequency noise have been numerically filtered by Fast Fourier Transform ("FFT") (the low frequency cutoff was set at $-2.896$ μm$^{-1}$ and the high frequency cutoff was set at $-217.1\ 96$ μm$^{-1}$). Theoretical interference patterns were calculated in accordance with Equation 1 and are identified in FIG. 6 as reference numerals 202-2, 204-2, 206-2, and 208-2. Specifically, reference numerals 202-1 and 202-2 respectively correspond to the observed and simulated measurements for a slit-slit separation distance of 20.98 μm; reference numerals 204-1 and 204-2 respectively correspond to the observed and simulated measurements for a slit-slit separation distance of 15.73 μm; reference numerals 206-1 and 206-2 respectively correspond to the observed and simulated measurements for a slit-slit separation distance of 13.12 μm; and reference numerals 208-1 and 208-2 respectively correspond to the observed and simulated measurements for a slit-slit separation distance of 10.50 μm.

As shown in FIG. 6, the theoretical predictions are in accordance with the measurement thereby confirming the occurrence of SPP-mediated spectral interference from interfaces 106 and 108. Consequently, FIG. 6 demonstrates that air/Ag/glass interfaces are able to support several different interference patterns including, but not limited to, the SPP modes on interface 106 or interface 108, which can both interfere with free space light and introduce interference patterns with higher modulation frequencies. High frequency interference patterns were also observed in the wavelength region between 700 nm and 800 nm. The amplitude of the interference signal is optimized by balancing the intensity of the two SPP modes, which are related to the coupling efficiencies for the two SPP modes at interfaces 106 and 108 in VPMZI 100.

The VPMZI disclosed herein advantageously provides a high sensitivity for optical sensing that has the potential for a one-to-two order-of-magnitude improvement over conventional nanoaperture arrays. Additionally, the VPMZI provides a compact sensing package that may be integrated into sensitive biosensing platforms and subwavelength optics on a chip. For example, a VPMZI may be integrated into a microfluidic channel to observe SPP interference in a liquid environment. The VPMZI disclosed herein advantageously enable sensitive SPR sensing applications to be performed with simple optical microscope systems compared to the complex conventional instrumentation that utilizes near-field scanning microscopes, leakage radiation microscopes, and prism-based SPR setups.

Although the invention has been described in terms of exemplary embodiments, it is not limited thereto. Rather, the appended claims should be construed broadly, to include other variants and embodiments of the invention, which may be made by those skilled in the art without departing from the scope and range of equivalents of the invention.

What is claimed is:

1. An optical device, comprising:
a first optical branch formed at an interface between a first substrate and a second substrate; and
a second optical branch formed at an interface between the second substrate and an ambient medium,
wherein the second substrate defines first and second spaced apart slits that are each coupled to the first and second optical branches, the first slit configured to receive at least partially coherent light from a broad bandwidth white light source and in response excite at least one surface plasmon polariton mode in each of the first and second optical branches, and the second slit configured to combine the surface plasmon polariton modes received from the first and second optical branches and emit scattered light into at least one of the first substrate and the ambient medium;
wherein the surface plasmon polariton modes received from the first and second optical branches constructively and destructively interfere with each other at the second slit;
wherein the slit separation is at a distance for white light to maintain coherence before detection by a detector.

2. The optical device of claim 1, wherein the first substrate includes a glass and the second substrate includes a metal.

3. The optical device of claim 1, wherein the ambient medium is air.

4. The optical device of claim 1, wherein the ambient medium is a liquid.

5. The optical device of claim 1, wherein the partially coherent light from the light source is received on a surface of the first substrate that is opposite the interface between the first and second substrates.

6. The optical device of claim 1, wherein the light emitted by the second slit is received by a detection device disposed adjacent to the interface between the second substrate and the ambient medium.

7. The optical device of claim 1, wherein a difference between a refractive index of the first substrate and a refractive index of the ambient medium is 0.03 or less.

8. The optical device of claim 1, wherein the broad bandwidth white light source is a halogen lamp.

9. The optical device of claim 1, wherein a difference between a refractive index of the first substrate and a refractive index of the ambient medium is 0.01 or less.

10. An optical device, comprising:
a broad bandwidth white light source;
a first substrate having opposed first and second surfaces, the first substrate configured to transmit light received from the white light source at the first surface to the second surface; and
a second substrate having opposed third and fourth surfaces, the third surface of the second substrate disposed on the second surface of the first substrate to define a first interface, the fourth surface of the second substrate defining a second interface with an ambient medium, and the second substrate defining spaced apart first and second slits that extend front the third surface to the fourth surface,
wherein the first slit is configured to excite at least one first surface plasmon polariton mode along a first optical transmission path defined by the first interface and at least one second surface plasmon polariton mode along a second optical transmission path defined by the second interface in response to receiving the light from the white light source through the first substrate, the second slit configured to combine the at least one first and second surface plasmon polariton modes of the first and second interfaces received from the first slit and emit scattered light into at least one of the first substrate and the ambient medium;
wherein the at least one first and second surface plasmon polariton modes constructively and destructively interfere with each other at the second slit;
wherein the slit separation is at a distance for white light to maintain coherence before detection by a detector.

11. The optical device of claim 10, wherein the first substrate includes a glass and the second substrate includes a metal.

12. The optical device of claim 10, wherein the ambient medium is one of a gas or a liquid.

13. The optical device of claim 10, wherein the light received at the first surface is at least partially coherent.

14. The optical device of claim 10, wherein a difference between a refractive index of the first substrate and a refractive index of the ambient medium is 0.03 or less.

15. The optical device of claim 10, wherein the light is received at the first surface at an angle that is approximately orthogonal to the first surface of the first substrate.

16. The optical device of claim 10, wherein each of the at least one first and second surface polariton modes include a plurality of surface polariton modes.

17. The optical device of claim 10, wherein a difference between a refractive index of the first substrate and a refractive index of the ambient medium is 0.01 or less.

18. The optical device of claim 10, wherein the broad bandwidth white light source is a halogen lamp.

19. A method, comprising:
receiving at least partially coherent light at a first surface of a first substrate, wherein the light is generated by a broad bandwidth white light source;
transmitting the at least partially coherent light, from the first surface of the first substrate to a second surface of the first substrate;
exciting at least one first surface plasmon polariton mode along a first optical transmission path defined by an interface of the first substrate and a second substrate in response to receiving the partially coherent light at a first slit defined by the second substrate;

exciting at least one second surface plasmon polariton mode along a second optical transmission path defined by an interface of the second substrate and an ambient medium in response to receiving the partially coherent light at the first slit;

combining the at least one first and second surface plasmon polariton modes at a second slit defined by the second substrate, the first and second slits being spaced apart; and scattering the combined at least first and second plasmon polariton modes into at least one of the first substrate and the ambient medium;

wherein the at least one first and second surface plasmon polariton modes constructively and destructively interfere with each other at the second slit;

wherein the slit separation is at a distance for white light to maintain coherence before detection by a detector.

20. The method of claim 19, wherein the combined at least one first and second surface polariton modes are scattered into the first substrate and the ambient medium.

21. The method of claim 19, wherein the ambient medium is one of a gas or a liquid.

22. The method of claim 19, further comprising receiving the scattered light at a detection device.

23. The method of claim 19, wherein the first substrate includes a glass and the second substrate includes a metal.

24. The method of claim 19, wherein a difference between a refractive index of the first substrate and a refractive index, of the ambient medium is 0.03 or less.

25. The method of claim 19, wherein a difference between a refractive index of the first substrate and a refractive index of the ambient medium is 0.01 or less.

26. The method of claim 19, wherein the broad bandwidth white light source is a halogen lamp.

27. A vertical plasmonic Mach-Zehnder interferometer, comprising:

a first optical branch formed at an interface between a first substrate and a second substrate; and a second optical branch formed at an interface between the second substrate and an ambient medium, wherein the second substrate defines first and second spaced apart slits that are each coupled to the first and second optical branches, the first slit configured to receive at least partially coherent light from a broad bandwidth white light source and in response excite at least one surface plasmon polariton mode in each of the first and second optical branches, and the second slit configured to combine the surface plasmon polariton modes received from the first and second optical branches and emit scattered light into at least one of the first substrate and the ambient medium;

wherein a difference between a refractive index of the first substrate and a refractive index of the ambient medium is 0.03 or less;

wherein the surface plasmon polariton modes received from the first and second optical branches constructively and destructively interfere with each other at the second slit;

wherein the slit separation is at a distance for white light to maintain coherence before detection by a detector.

* * * * *